United States Patent [19]

Latman et al.

[11] Patent Number: 5,438,049
[45] Date of Patent: Aug. 1, 1995

[54] 16-EPIESTRIOL TO PREVENT, INHIBIT, OR REDUCE INFLAMMATION WITHOUT GLYCOGENIC EFFECTS

[76] Inventors: Neal S. Latman, 513 Bowie St., Borger, Tex. 79007; Virmal Kishore, 4632 Nottingham Dr., New Orleans, La. 70127; Brent C. Bruot, 620 Woodside Dr., Kent, Ohio 44240; Harold H. Flanders, 3310 Ault Dr., Amarillo, Tex. 79121

[21] Appl. No.: 105,391

[22] Filed: Aug. 12, 1993

[51] Int. Cl.⁶ ............................................. A67K 51/56
[52] U.S. Cl. .................................... 514/182; 552/617
[58] Field of Search .......................... 552/617; 514/182

[56] References Cited

U.S. PATENT DOCUMENTS 3,002,009  9/1961  Huffman ............................. 514/182
4,795,747  1/1989  Latman et al. ...................... 514/182

Primary Examiner—Johann Richter
Assistant Examiner—Kimberly J. Kestler
Attorney, Agent, or Firm—Harold H. Flanders

[57] ABSTRACT

A method for the treatment of inflammation, its signs and symptoms, in a mammal which comprises the administration of an anti-inflammatory effective amount of 16-epiestriol without glycogenic related adverse side-effects.

2 Claims, 2 Drawing Sheets

16-EPIESTRIOL TO PREVENT, INHIBIT, OR REDUCE INFLAMMATION WITHOUT GLYCOGENIC EFFECTS

FIELD OF THE INVENTION

The present invention relates to the discovery that 16-epiestriol has a high anti-inflammatory potency without significant glycogenic activity.

BACKGROUND

Physiologically active steroid molecules produced by the body are classified as either "glucocorticoid," "mineralocorticoid," or "sex steroid" depending on their specific activity. The glucocorticoid steroids are defined by the exhibition of two physiological actions-glycogenic and anti-inflammatory. They are glycogenic in that they effect the carbohydrate metabolism and increase gluconeogenesis and they are anti-inflammatory in that they prevent, inhibit, or reduce inflammation. (Ringler, I. "Activities of Adrenocorticosteroid in Experimental Animals and Man." in Dorfman, R. I. (Editor). "Methods in Hormone Research." Volume III, 1964. Academic Press, New York. and David, D. S. et al. 1970, J. Chron. Dis. 22:637–711.) The classification of "glucocorticoid" is usually dependent upon measurement of increased liver glucose concentrations, increased plasma glucose concentrations, and/or anti-inflammatory activity in response to the steroid. It has been found that the glycogenic activity parallels the anti-inflammatory activity of glucocorticoid steroids. (Ringler, I. "Activities of Adrenocorticosteroid in Experimental Animals and Man." in Dorfman, R. I. (Editor) "Methods in Hormone Research." Volume III. 1964. Academic Press, New York., Castles, J. J. "Glucocorticoid." in McCarty, D. J. (Editor). "Arthritis and Allied Conditions." Tenth Edition, 1985. Lea & Febiger, Philadelphia., Thomas, J. A. & Keenan, E. J. "Principles of Endocrine Pharmacology." 1986. Plenum Medical Book Co., New York., Haynes, R. C. "Adrenocorticotropic Hormone; Adrenocortical Steroids and Their Synthetic Analogs; Inhibitors of the Synthesis and Actions of Adrenocortical Hormones." in Gilman, A. G. et al. (Editors). "The Pharmacological Basis of Therapeutics." Eighth Edition. 1990. Pergamon Press, New York.)

All previously known steroid molecules, naturally occurring or synthetic, that have been shown to exhibit significant anti-inflammatory activity have also exhibited significant and parallel glycogenic activity. (Haynes, R. C. "Adrenocorticotropic Hormone; Adrenocortical Steroids and Their Synthetic Analogs; Inhibitors of the Synthesis and Actions of Adrenocortical Hormones." in Gilman, A. G. et al. (Editors). "The Pharmacological Basis of Therapeutics." Eighth Edition. 1990. Pergamon Press, New York., and Gill, G. N. "The Adrenal Gland". in West, J. B. (Editor). "Physiological Basis of Medical Practice." Twelfth Edition. 1991. Williams & Wilkins, Baltimore.) It has been thought that these two activities, glycogenic and anti-inflammatory, are firmly linked and it is unlikely that they could be dissociated by changing the chemical structure of the steroid molecule. (Bentley, P. J. "Endocrine Pharmacology." 1980. Cambridge University Press, New York.) Since no substantial progress has previously been reported toward separation of these two activities, it is generally held that they are only different physiological expressions of a common mechanism of action, Since there is experimental evidence suggesting that a single mechanism is responsible for both activities, it has been held unlikely that this long sought after separation of activities could be achieved. (Castles, J. J. "Glucocorticoid." in McCarty, D. J. (Editor). "Arthritis and Allied Conditions." Tenth Edition. 1985. Lea & Febiger, Philadelphia., and Popper, T. L. and Watnick, A. S. "Anti-inflammatory Steroids." in Scherrer, R. A. and Whitehouse, M. W. (Editors). "Anti-inflammatory Agents." Volume I. 1974. Academic Press, New York.)

The major problem with the glucocorticoid as anti-inflammatory agents, however, is their glycogenic activities. These glycogenic adverse side-effects are simply the exaggerated responses to the pharmacologic (supra-physiological) doses. The ideal anti-inflammatory steroid would not exhibit glycogenic activity. The prior art does not permit this anti-inflammatory activity without glycogenic activity.

Since some of the major adverse side-effects of the glucocorticoid are the anticipated glycogenic actions of the supra-physiologic doses, the prior art of their use has resulted in the following six problems or limitations of use: 1.) frequent occurrence of significant adverse side-effects, 2.) limitations of dosage, 3.) limitation of duration of use, 4.) contraindication for use in certain specific groups of people, 5.) reduced frequency of use, and 6.) restricted route of administration.

Commonly observed adverse side-effects can include the following: adrenal suppression; hyperglycemia and glycosuria ("steroid diabetes mellitus"); myopathy; osteoporosis; skin atrophy; redistribution of body fat (e.g. "buffalo hump"); and delayed wound healing. (Haynes, R. C. "Adrenocorticotropic Hormone." in Gilman, A. C. et al (Editors). "The Pharmacological Basis of Therapeutics." 1990. Pergamon Press, New York; Thomas, J. A. and Keenan, E. J. "Principles of Endocrine Pharmacology." 1986. Plenum Medical Book Co., New York; Bentley, P. J. "Endocrine Pharmacology." 1980. Cambridge University Press, New York; Hart, D. F. "Drug Treatment of the Rheumatic Diseases." 1979. Adis Press, New York.) This is primarily iatrogenic hypercortisolism. In fact, the most common cause of hypercortisolism is the therapeutic use of glucocorticoid. It had been estimated in 1968 that the glucocorticoid were probably the cause of more iatrogenic diseases than any other group of drugs. One estimate of all therapeutic drug deaths in England attributed 20% to the glucocorticoid. (Bentley, P. J. "Endocrine Pharmacology." 1980. Cambridge University Press, New York.)

In an effort to reduce these severe adverse side-effects, the dosage of the glucocorticoid steroids is reduced as much as possible for prolonged use. For example, the initial dose of prednisone, a typical glucocorticoid commonly used in treating inflammation, may be 10 mg/day. But the maintenance dosage may not be greater than 7.5 mg/day. (Weiss, M. M. 1989. Seminars in Arthritis and Rheumatism. 19:9–21.) It is generally accepted that if a dosage of prednisone exceeds 6 to 7 mg/day some adverse side-effects will be exhibited. A dosage of 10 rag/day will invariably result in side-effects within a few weeks or months. (Hart, D. F. "Drug Treatment in the Rheumatic Diseases." 1979. Adis Press, New York.) Therefore, the dosage of glucocorticoid used is limited by the occurrence of adverse side-effects, thus limiting the anti-inflammatory efficacy.

Even very low doses of glucocorticoid administered over prolonged periods of time may have adverse side-effects. It is thought, therefore, that deleterious effects are the result of the total cumulative dose. (Weiss, M. M. 1989. Seminars in Arthritis and Rheumatism. 19:9–21.) Therefore the duration of treatment can be limited by the adverse side-effects. The dose and duration of treatment with glucocorticoid parallel the incidence and severity of adverse side-effects. (Bentley, P. J. "Endocrine Pharmacology." 1980. Cambridge University Press, New York; Castles, J. J. "Glucocorticoid." in McCarty, D. J. (Editor) "Arthritis and Allied Conditions." 1985. Lea & Febiger, Philadelphia.) Therefore, the duration of use of glucocorticoid is limited by the adverse side-effects, thus limiting the anti-inflammatory efficacy.

As a result of pre-existing conditions, the use of glucocorticoid as anti-inflammatory agents are contraindicated in certain individuals. This is often due to the glycogenic activity of the glucocorticoid. Their use is contraindicated due to the glycogenic activity in people with such conditions as the following: diabetes mellitus, osteoporosis, pregnancy, growing children, wound healing, and Cushing's syndrome. (Thomas, J. A. and Keenan, E. J. "Principles of Endocrine Pharmacology." 1986. Plenum Medical Book Co., New York; Bentley, P. J. "Endocrine Pharmacology." 1980. Cambridge University Press, New York; Weiss, M. M. 1989. Seminars in Arthritis and Rheumatism. 19:9–21; Castles, D. J. "Glucocorticoid ." in McCarty, D. J. (Editor) "Arthritis and Allied Conditions." 1985. Lea & Febiger, Philadelphia.) Therefore, even the use of glucocorticoid is contraindicated in some people, thus denying them access to potent anti-inflammatory efficacy.

One method used in the prior art to reduce the incidence and severity of adverse side-effects of glucocorticoid is "Alternate-day dose regimen." Another method is the "single morning dose regimen." These methods of periodic, intermittent, or pulse dosing may reduce some of the glycogenic related adverse side-effects in some, but not all people. In addition, they may reduce the anti inflammatory efficacy of the drug. (Haynes, R. L. "Adrenocorticotropic Hormone": in Gilman, A. G. et al (Editors) "The Pharmacological Basis of Therapeutics." 1990. Pergamon Press, New York; Popper T. L. and Watnick, A. S. "Anti-inflammatory Steroids." in Scherrer, R. A. and Whitehouse, M. W. "Anti-inflammatory Agents." 1974. Academic Press, New York; Hart, F. D. "Drug Treatment of the Rheumatic Diseases." 1979. Adis Press, New York; Bentley, P. J. "Endocrine Pharmacology." 1980. Cambridge University Press, New York; Castles, J. J. "Glucocorticoid." in McCarty, D. J. "Arthritis and Allied Conditions." 1985. Lea & Febiger, Philadelphia.)

Changing the route of administration of glucocorticoid has been used in an effort to reduce the potential for systemic adverse side-effects. While local injections have been used to reduce systemic glycogenic related complications, they have simultaneously increased the probability for other severe adverse side-effects. In addition, local injections continue to produce local adverse side effects related to the glycogenic activity. (Popper, T. L. and Watnick, A. S. "Anti-inflammatory Steroids." in Scherrer, R. A. and Whitehouse, M. W. (Editors) "Anti-inflammatory Agents." 1974. Academic Press, New York; Weiss, M. M. 1989. Seminars in Arthritis and Rheumatism. 19:9–21; David, D. S., Grieco, M. H., and Cushman, P. 1970. J. Chron. Dis. 22:637–711; Hart, D. F. "Drug Treatment of the Rheumatic Diseases." 1979. Adis Press, New York.) Therefore, the route of administration of glucocorticoid is often limited by adverse side-effects, thus limiting the anti-inflammatory efficacy.

A previous patent (U.S. Pat. No. 4,795,747) demonstrated that 16-epiestriol exhibited significant anti-inflammatory activity. Its molecular structure, however, contained none of the four structural elements considered by the prior art essential for anti-inflammatory activity.

SUMMARY OF INVENTION

Accordingly, it is an object of this present invention to separate the anti-inflammatory activity of a steroid, 16-epiestriol, from the glycogenic activity and thereby provide an anti-inflammatory steroid that will not cause the adverse side-effects associated with glycogenic activity.

It is a further objective to provide a drug without glycogenic activity for use in treating the inflammatory signs and symptoms of rheumatoid arthritis and other diseases and conditions or pathologies with an inflammatory component.

Other objectives and a fuller understanding of the present invention may be had by referring to the following description and claims taken in conjunction with the accompanying drawings and tables.

The present invention overcomes the deficiencies of the prior art and achieves its objective by employing 16-epiestriol as an anti-inflammatory agent without glycogenic activity.

BRIEF DESCRIPTION OF THE DRAWINGS

In order to facilitate the understanding of the present invention reference will now be made to the appended figures. These figures should not be construed as limiting the invention, but is exemplary only. These figures.

FIG. 1 represents Glycogenic Activity Test I—Plasma Glucose Concentration.

FIG. 2 represents Glycogenic Activity Test II—Liver Glucose Concentration.

In both figures, mean values are +/− S.E. and N.S. indicates "not significantly different".

DESCRIPTION OF THE PREFERRED EMBODIMENT

The chemical compound 16-epiestriol, the new use of which is the subject of the present invention, is a known compound and is described at Entry 3565 of the 10th edition of the Merck Index.

The compound is know as Estra- 1,3,5( 10)-triene-3,16B,17B-triol: 1,3,5 estratriene-3,16B,17B,-triol; 16-epiestriol; or as Actriol. The compound has the empirical formula:

$C_{18}H_{24}O_3$

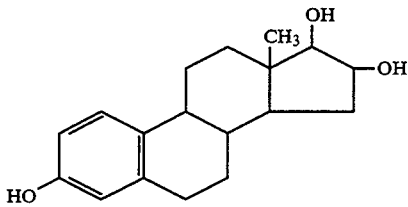

It is further known as 16B-estriol; 1,3,5 ,( 10)-estratriene-3, 16B, 17B-triol; 3,16B,17B-trihydroxy Δ 1,3,5-estratriene; and trihydroxy-estrin(16B).

The method of isolation and synthesis of the compound and its chemical and physical properties are described in Marrian and Bauld [Biochem. J. 58, xxvi (1954); 59, 136 (1955)]; Watson, Marrian, idib. 63, 64 (1956); Diezfalusy, Halla, Acta Endocrinol. 27, 303 (1958); Biggerstaff, Gallagher, J. Org. Chem. 22, 1220 (1957) Huffman [J.A.C.S. 66, 150 (1944); 69, 1835 (1947)]; Huffman, Gollman [Endocr.41, 12 20 (1947)]and U.S. Pat. No. 3,002,009 issued Sep. 26, 1961 to Maz M. Huffman.

The anti-inflammatory activity was demonstrated in U.S. Pat. No. 4,795,747 by Latman et al. The absence of glycogenic activity for 16-epiestriol was confirmed in the course of the following described experiments.

EXAMPLES

Three groups of adrenalectomized rats with a body weight of approximately 200 grams per animal were administered 4 sub-cutaneous injections at 2 hour intervals as follows:

Group one—85% water, 5% glucose, and 10% ethanol. (The Carrier Vehicle.) 0.2 milliliters/injection.

Group two—60 micrograms of cortisol in 0.2 milliliters of carrier vehicle per injection per animal.

Group three—60 micrograms of 16-epiestriol in 0.2 milliliters of carrier vehicle per injection per animal.

The test was administered in accordance with the following protocol:

All rats were adrenalectomized on "Day 1."On the evening of "Day 6" all access to food was removed. On the morning of "Day 7" each animal was given a sub-cutaneous injection of the appropriate dose as described above at experimental "Time 0" and again at 2 hour intervals for a total of 4 injections per animal. Therefore, injections were given each animal at experimental times "0", 2,4, and 6, hours. At "8" hours experimental time, samples of liver and blood were collected from each animal. The glucose concentrations of the liver and plasma were measured.

Figure 1:
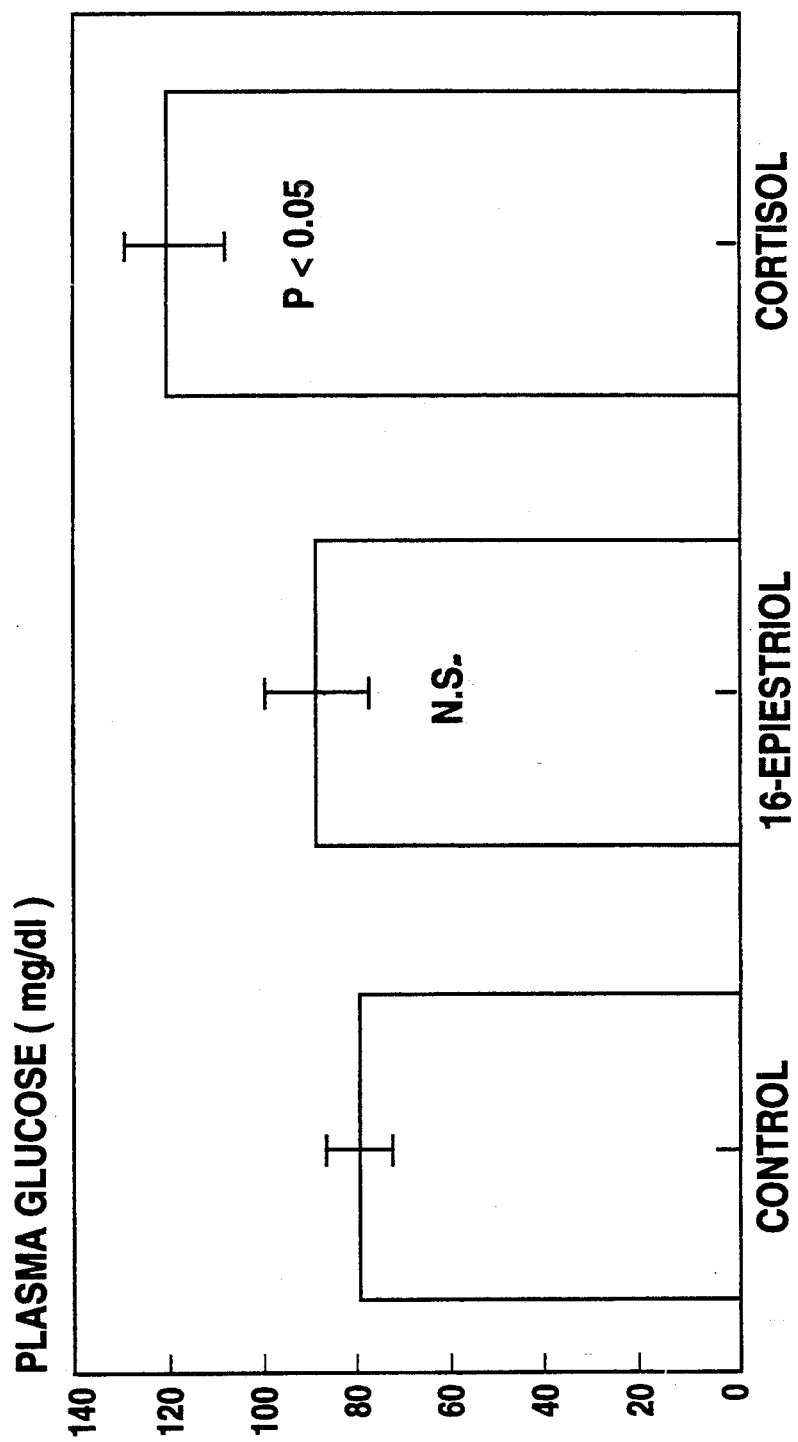
FIG. 1 and FIG. 2, show the absence of glycogenic activity of 16 epiestriol, this absence of glycogenic activity being demonstrated by a lack of statistically significant differences in liver glucose and/or plasma glucose concentration in animals treated with this agent compared to those not treated, and statistically significantly less than those treated with the same dose of cortisol, a typical glucocorticoid, in the adrenalectomized rat model.
Figure 2:
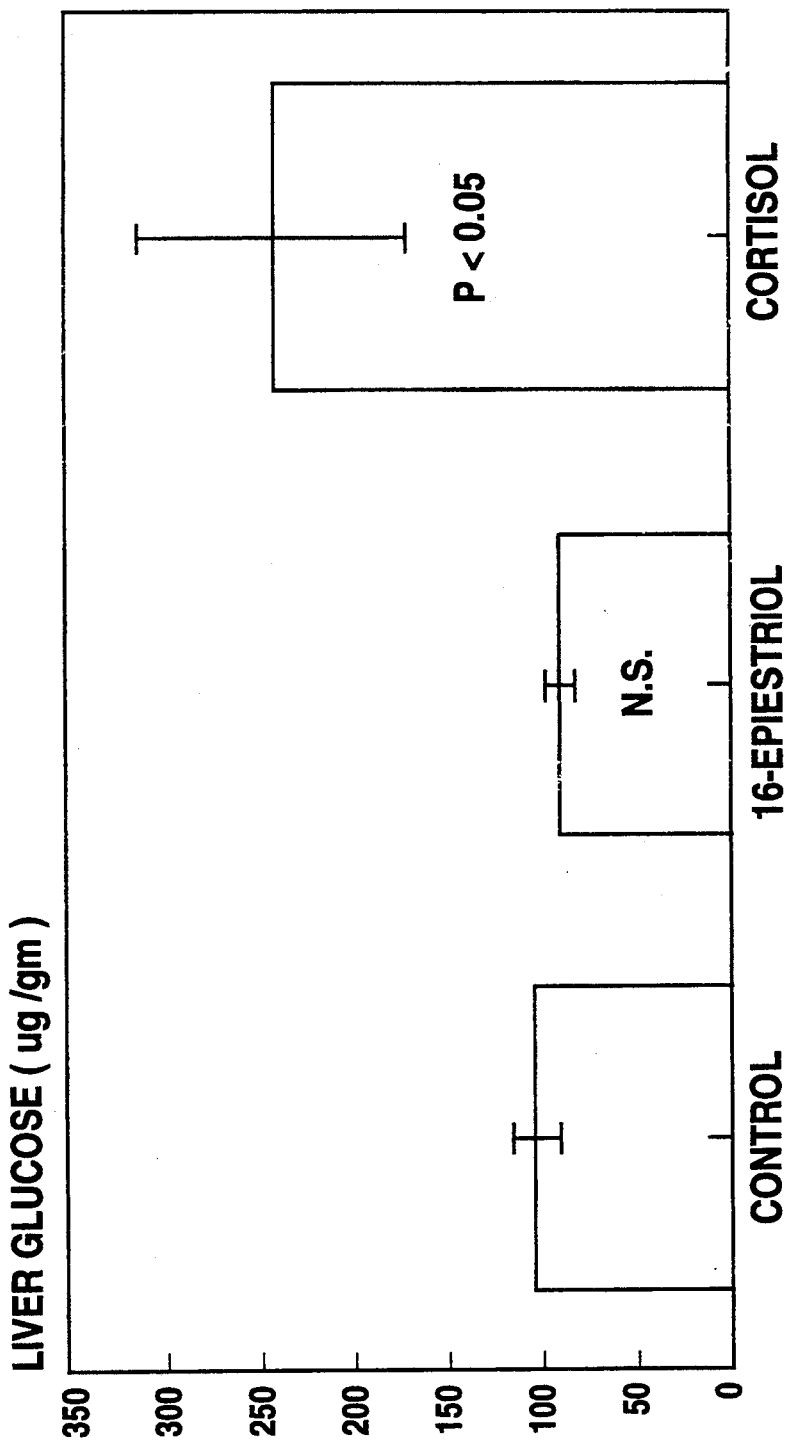

The figures, FIG. 1 and FIG. 2, illustrate the glucose concentration in the liver and plasma for the untreated controls, the cortisol treated, and the 16 epiestriol treated animals. The results are indicated in Table I with their statistical significance.

TABLE 1

| Glycogenic Activity Tests of 16-Epiestriol | | |
|---|---|---|
| Test Substances | Plasma Glucose Median mg/dl | Liver Glucose Median ug/gm |
| Control | 74.6 | 102 |
| 16-Epiestriol | 79.4(N. S.) | 93.9(N. S.) |
| Cortisol | 112.6* | 133.8** |

N. S. = not statistically significant
* = p < 0.004 by Mann-Whitney U-Test
** = p < 0.01 by Mann-Whitney U-Test It will be noted that cortisol significantly increased the glucose concentration in the liver and the plasma as expected by the prior art. The 16-epiestriol treated animals exhibited no significant increase in liver or plasma glucose concentration when compared to the untreated control animals. The above data clearly demonstrated the absence of glycogenic activity exhibited by 16-epiestriol and, therefore, strongly indicates it lack of potential to induce glycogenic related adverse side-effects from the use of 16 epiestriol as an anti-inflammatory agent.

The administration of 16-epiestriol to provide anti-inflammatory activity without or with reduced glycogenic activity could be achieved by several methods. 16-Epiestriol could be administered as the only active anti-inflammatory agent. This would provide a potent anti-inflammatory effect with no glycogenic effect. An alternative method would be to administer 16-epiestriol in combination with a glucocorticoid anti-inflammatory steroid(s). This could, depending on the glucocorticoid chosen, provide greatly increased anti-inflammatory effect with a greatly reduced glycogenic effect; a reduced anti-inflammatory effect, with a greatly reduced glycogenic effect; or an equal anti-inflammatory effect, with greatly reduced glycogenic effect. The specific effect depending, among other factors, on the specific glucocorticoid(s) chosen and the proportion of glucocorticoid/16-epiestriol in the mixture. The advantages of this method are most readily expressed as a benefit/risk ratio, derived by dividing the relative anti-inflammatory effect (the benefit) by the relative glycogenic effect (the risk). As the ratio increases the anti-inflammatory benefit increases relative to the glycogenic adverse risk. (The relative anti-inflammatory and glycogenic activities of the glucocorticoid used in these calculations are exemplary only and based on Ringler, I. "Activities of adrenocaorticosteroids in Experimental Animals and Man." in Dorfman, R. I. (Editor). "Methods in Hormone Research." Volume III, 1964. Academic Press, New York., Fried, J. and Borman, A. 1958. Vitamins and Hormones. 16:303–374, and Wolff, M. E. "Anti-inflammatory Steroids." in Wolff, M. E. (Editor) "Burger's Medicinal Chemistry." 1981. John Wiley & Sons, New York.) The effect on the benefit/risk ratio at different proportional mixtures is illustrated in Table 2. The effect on the benefit/risk ratio combining 16-epiestriol with various glucocorticoid is illustrated in Table 3. As can be seen by tables 2 & 3, mixing 16-epiestriol with a glucocorticoid(s) results in higher (improved) benefit/risk ratios. These tables are intended as illustrative only and are not intended to limit either the glucocorticoid with which 16 epiestriol could be mixed, the proportions of such mixtures, or the precise or exact benefit/risk ratio that might result.

Table 2. Affecting a change in the anti-inflammatory benefit/adverse glycogenic risk ratio by combining 16-epiestriol with glycocorticoids in varying proportions. The relative anti-inflammatory and glycogenic activity is expressed as relative to cortisol as the standard. (See Table 2)

TABLE 2

| Gluco-Corticoid | Benefit/Risk Ratio | Combination* % 16-Epiestriol | Combined Benefit/ Risk Ratio |
|---|---|---|---|
| Cortisol | 1 | 25 | 2 |
| Cortisol | 1 | 50 | 5 |
| Cortisol | 1 | 75 | 12 |
| Cortisol | 1 | 90 | 37 |

TABLE 2-continued

| Gluco-Corticoid | Benefit/Risk Ratio | Combination* % 16-Epiestriol | Combined Benefit/Risk Ratio |
| --- | --- | --- | --- |
| Triamcinolone | 2 | 25 | 2.7 |
| Triamcinolone | 2 | 50 | 4 |
| Triamcinolone | 2 | 75 | 8 |
| Triamcinolone | 2 | 90 | 20 |

*% 16-Epiestriol combined with a glucocorticoid

Table 3. Affecting the anti-inflammatory benefit/adverse glycogenic risk ratio by combining 16-epiestriol with various glucocorticoid. The relative anti-inflammatory and glycogenic activity is expressed relative to cortisol as the standard. (See Table 3)

TABLE 3

| Gluco-Corticoid | Benefit/Risk Ratio | Combination* % 16-Epiestriol | Combined Benefit/Risk Ratio |
| --- | --- | --- | --- |
| Cortisol | 1 | 50 | 5 |
| Prednisolone | 1 | 50 | 2.3 |
| 9-Fluoroprednisolone | 0.7 | 50 | 0.85 |
| 9-Fluorocortisol | 0.7 | 50 | 1.25 |
| 16-Methylcortisol | 6.6 | 50 | 13.3 |
| 6-Fluorocortisol | 0.8 | 50 | 1.2 |
| 2-Methylcortisol | 0.5 | 50 | 1.2 |
| Triamcinolone | 2 | 50 | 4 |

*% 16-Epiestriol combined with a glucocorticoid

The application of 16-epiestriol as an anti-inflammatory agent without glycogenic activity could take the form of derivatives such as:

16-epiestriol-17-acetate;
16-epiestriol-16,17-diacetate;
16-epiestriol-3,16,17-triacetate;
16-epiestriol-16,17 dipropionate;
16-epiestriol-17 pivalate;
16-epiestriol-17-cypionate;
16-epiestriol- acetonide;
16-epiestriol-sodium succinate;
16-epiestriol-sodium phosphate; and any and all other derivatives.

The 16-epiestriol or derivative is administered in an antiinflammatory amount by any convenient or appropriate method.

Preferred methods of administration are, topically, orally, subcutaneous injections or implantation, intramuscular injections, intra articular injections, transcutaneous, and other routes. The effective amound is administered in a pharmaceutically safe formulation with a carrier.

Dosages for administration according to this invention may be compound into oral dosage forms such as tablets, capsules, and the like. This done by combining the compounds with conventual carriers and other excipient, such as magnesium carbonate, magnesium stearate, talc, sugar, lactose, pectin, dextrin, starch, gelatin, tragacanth, methyl cellulose, sodium carbocy methyl cellulose, low melting wax, cocoa butter, and the like. Diluents, flavoring agents, binders, tablet-disintegrating agents and the like may also be compounded with the compositions of the present invention. Active ingredients in these compositions, whether solid or liquid, will be at least sufficient to impart antiinflammatory activity in vivo after oral or parenteral or topical or other routes of administration.

The dosage requirements vary with the particular compositions employed, the route of administration, the severity of symptoms present, and the particular subject being treated. Treatment will generally be initiated with small dosages less than the optimum dose of the compound. Throughout, the dosage my be increased until the optimum effect under the circumstances is reached. In general, the tangible embodiments of invention are most desirably administered at a concentration(s) that will generally afford effective results without causing any harmful or deleterious effects. The dose will vary depending on these and other such factors which a person skilled in the art will recognize.

Although a specific preferred embodiment of the present invention has been described in the detailed description above, the description is not intended to limit the invention to any particular forms or embodiment disclosed herein, since they are to be recognized as illustrative rather than restrictive. It will be obvious to those skilled in the art that the invention is not so limited. The invention is declared to cover all changes and modifications of the specific examples of the invention herein disclosed for purpose of illustration which do not constitute departure from the spirit and scope of the present invention.

What is claimed is:

1. A method of treating inflammation by administering 16-epiestriol as an anti-inflammatory agent, alone or in combination with one or more gluccocorticoids, wherein it is administered to individuals with diabetes mellitus, osteoporosis, severe wounds, pregnancy, continuing growth or other conditions which would limit the use of anti-inflammatory agents with glycogenic activities and wherein the glygogenic related adverse side-effects of the gluccocorticoid(s) are reduced, resulting in a higher anti-inflammatory benefit/glycogenic risk ratio by the use of 16-epiestriol.

2. A method for the administration of 16-epiestriol in combination with one or more glucocorticoid wherein the glycogenic related adverse side-effects of the glucocorticoid(s) is reduced resulting in a higher antiinflammatory benefit/glycogenic risk ratio.

* * * * *